(12) United States Patent
Chapuis et al.

(10) Patent No.: US 6,348,692 B1
(45) Date of Patent: Feb. 19, 2002

(54) DEVICE AND METHOD FOR NUCLEAR LOCATING BY ITERATIVE COMPUTING OF BARYCENTER, AND APPLICATION TO GAMMA-CAMERAS

(75) Inventors: Alain Chapuis, St Martin le Vinoux; Claude Janin, Grenoble; Michel Tararine, Sceaux, all of (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/331,401
(22) PCT Filed: Dec. 29, 1997
(86) PCT No.: PCT/FR97/02436
  § 371 Date: Sep. 14, 1999
  § 102(e) Date: Sep. 14, 1999
(87) PCT Pub. No.: WO98/29763
  PCT Pub. Date: Jul. 9, 1998

(30) Foreign Application Priority Data

Dec. 31, 1996 (FR) ............................. 96 16295

(51) Int. Cl.⁷ .......................... G01T 1/208; G01T 1/164
(52) U.S. Cl. ...................................................... 250/369
(58) Field of Search .............................. 250/369, 370.1, 250/370.11, 366, 363.02, 363.03

(56) References Cited

U.S. PATENT DOCUMENTS

| 3,011,057 A | | 11/1961 | Anger |
| 4,060,730 A | | 11/1977 | Zioni et al. |
| 4,611,283 A | | 9/1986 | Lumelsky et al. |
| 4,672,542 A | | 6/1987 | Roux et al. |
| 4,881,171 A | * | 11/1989 | Jatteau et al. ........... 250/363.02 |
| 5,185,259 A | * | 2/1993 | Smith et al. ................. 250/369 |
| 5,371,362 A | | 12/1994 | Mestais et al. |
| 5,444,253 A | * | 8/1995 | Berlad ......................... 250/369 |
| 5,504,334 A | * | 4/1996 | Jansen et al. ................ 250/369 |
| 5,576,547 A | * | 11/1996 | Ferriera et al. .............. 250/369 |
| 5,952,662 A | * | 9/1999 | McDaniel .................... 250/369 |
| 6,057,551 A | * | 5/2000 | Tararine ................. 250/363.03 |

FOREIGN PATENT DOCUMENTS

| EP | 0 634 672 A1 | 1/1995 |
| FR | 0 252 566 | 1/1988 |
| FR | 2 669 439 | 5/1992 |

\* cited by examiner

*Primary Examiner*—Constantine Hannaher
*Assistant Examiner*—Albert Gagliardi
(74) *Attorney, Agent, or Firm*—Burns Doane Swecker & Mathis LLP

(57) ABSTRACT

The invention relates to a process for determining the position of an event with respect to a set of N photodetectors, comprising the following after digitization of the signal output by each photodetector:
  calculate an uncorrected position of the event,
  determine the distance of each photodetector from the uncorrected position,
  calculate a corrected value of the contribution of each photodetector as a function of the distance from P0,
  calculate a new position P1, as a function of the corrected contributions of the photodetectors and their position.

Another purpose of the invention is a device for embodiment of the process.

24 Claims, 11 Drawing Sheets

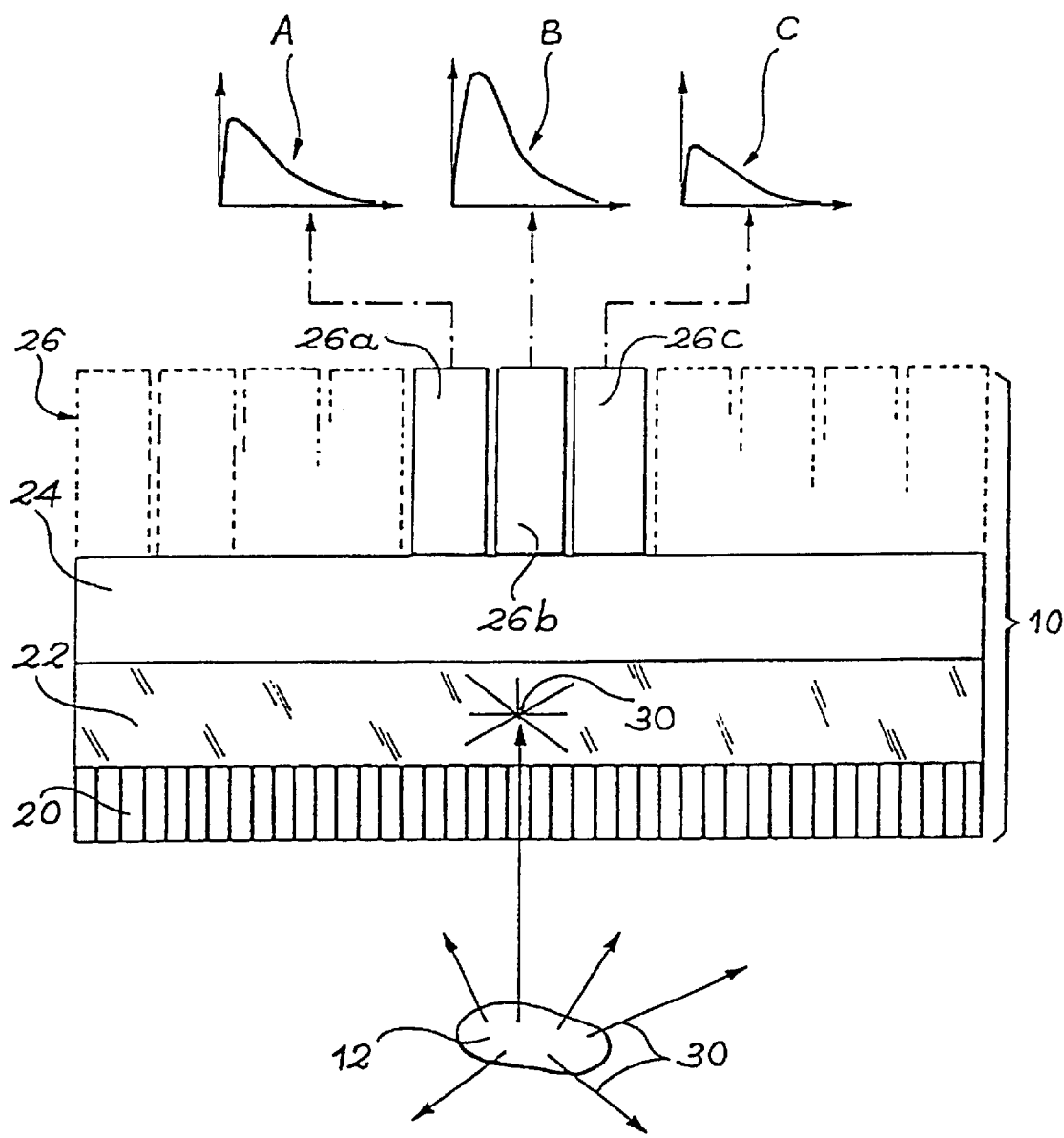
FIG._1
*(PRIOR ART)*

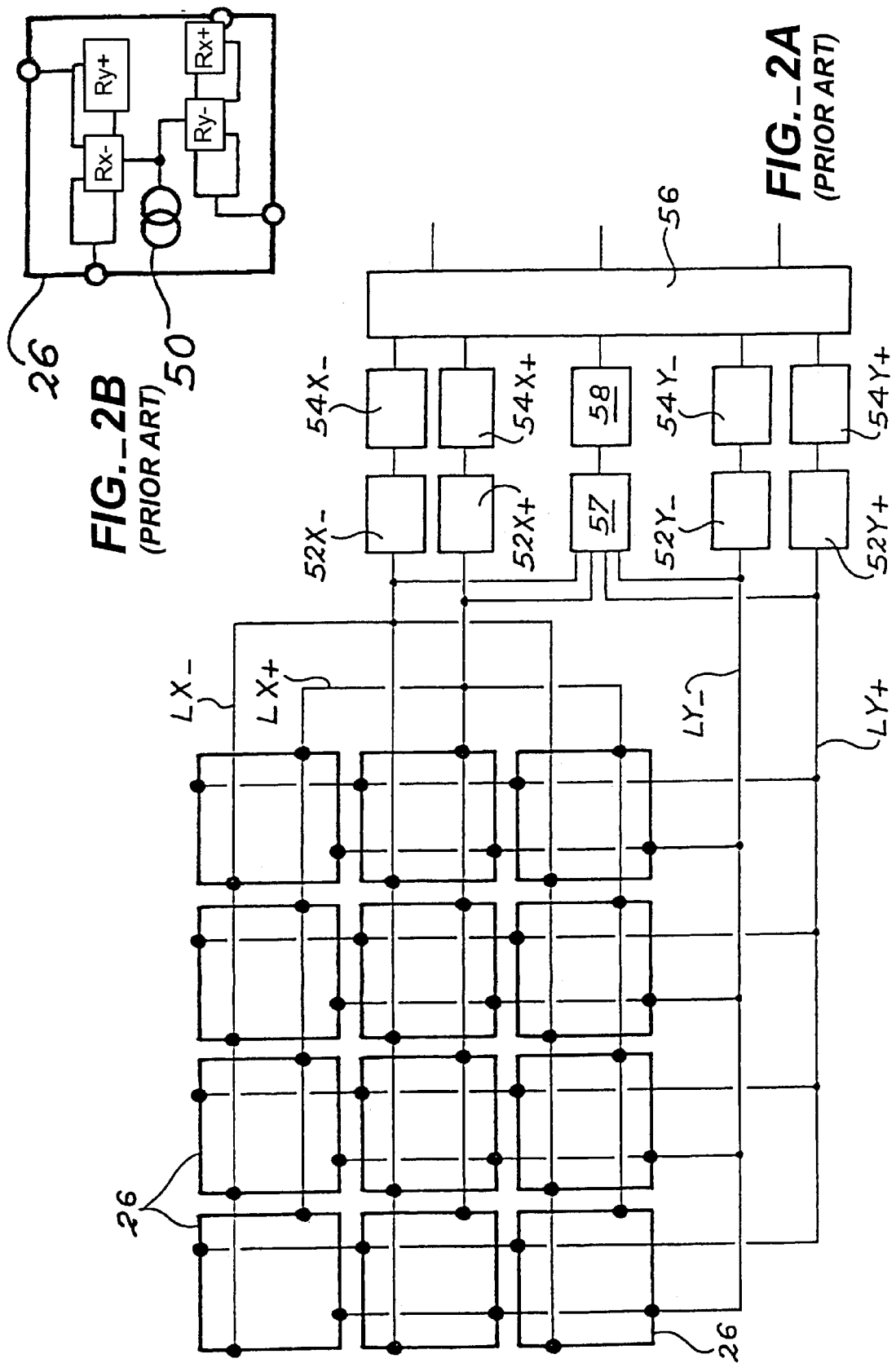
FIG._2A (PRIOR ART)
FIG._2B (PRIOR ART)

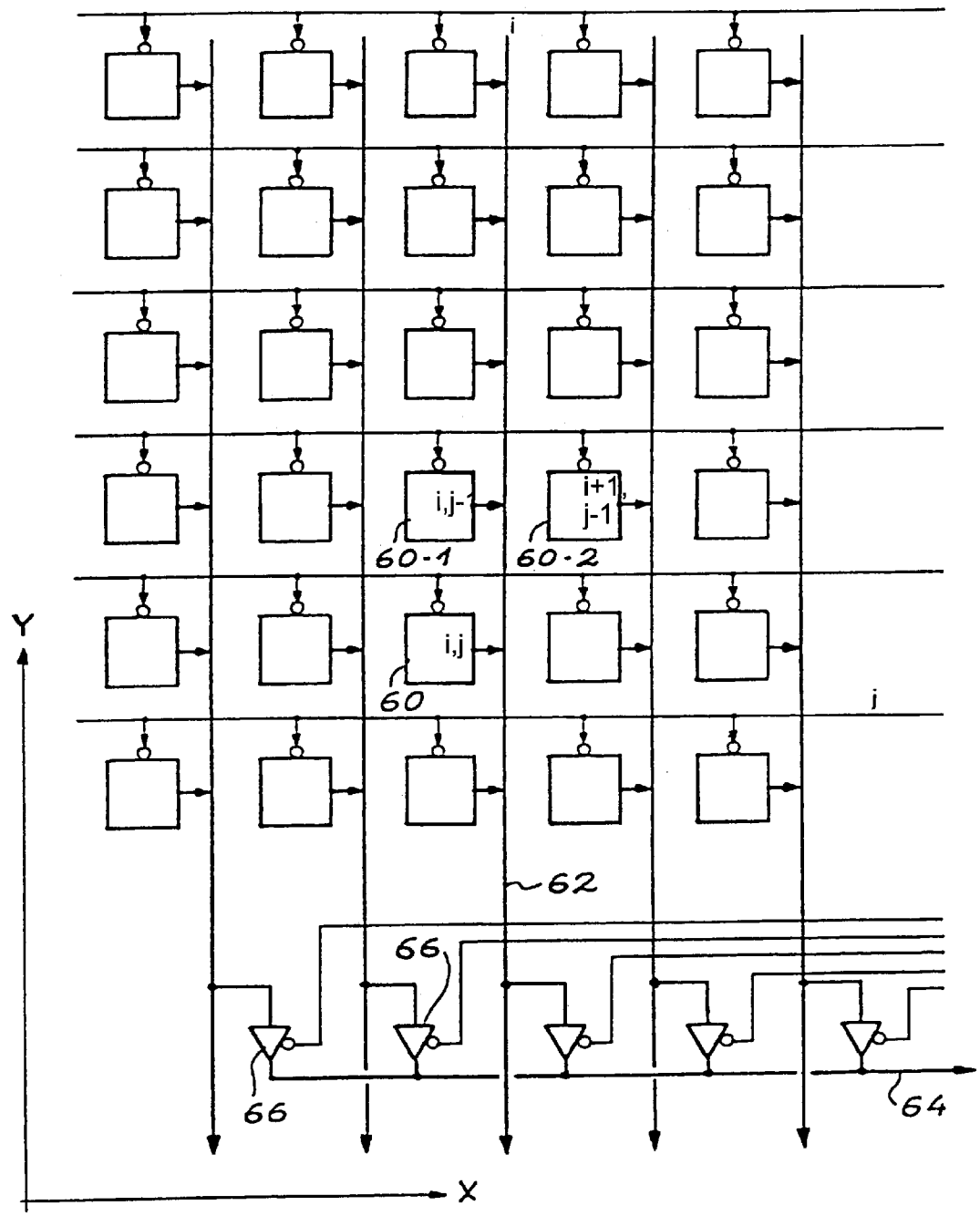
FIG._3

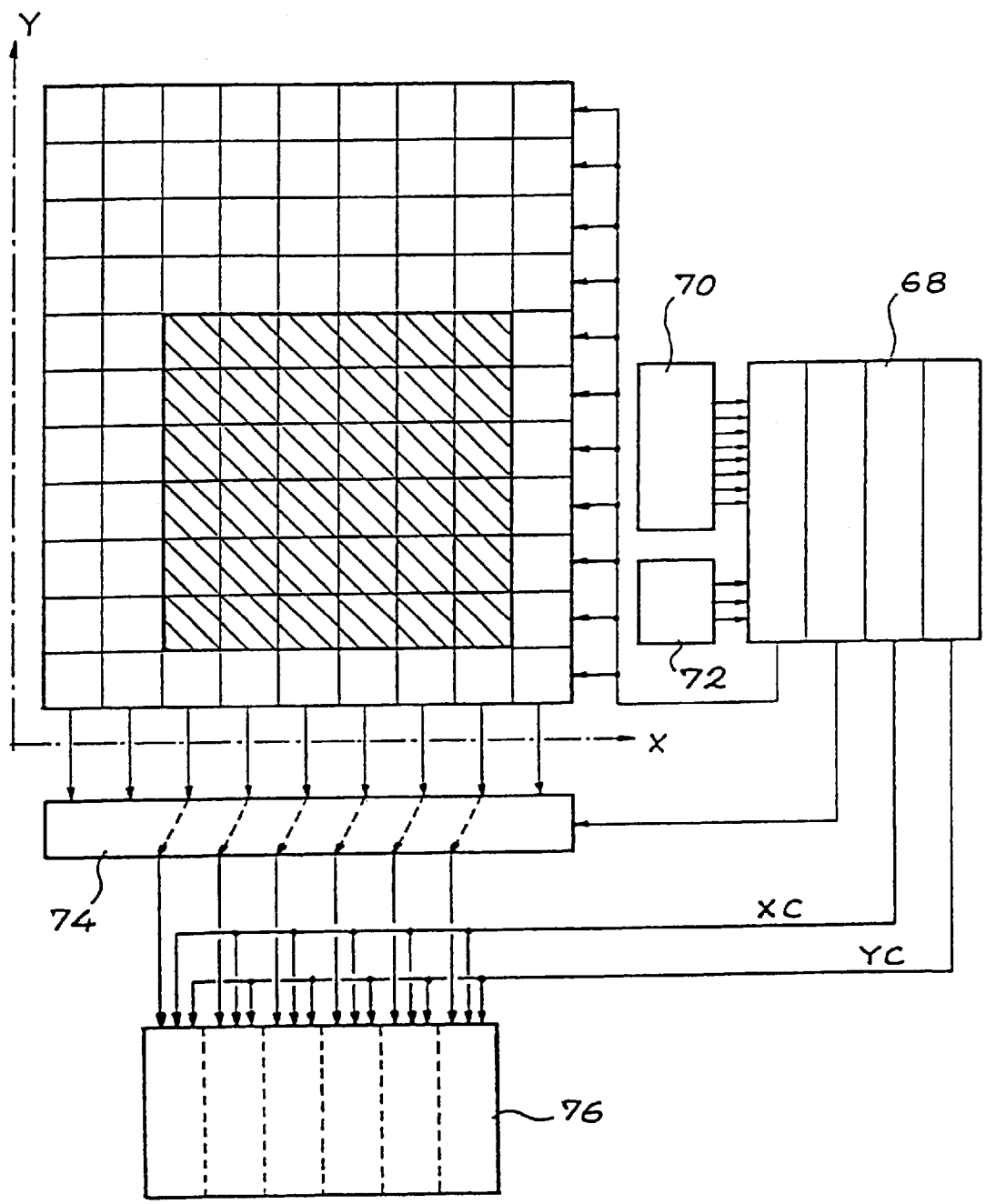
FIG._4

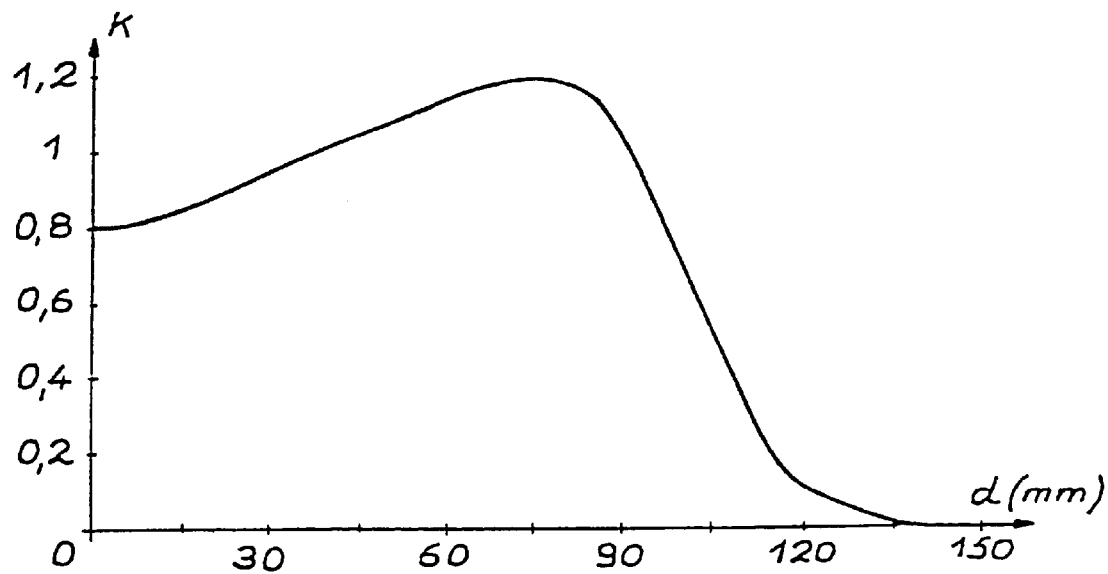
FIG._5A
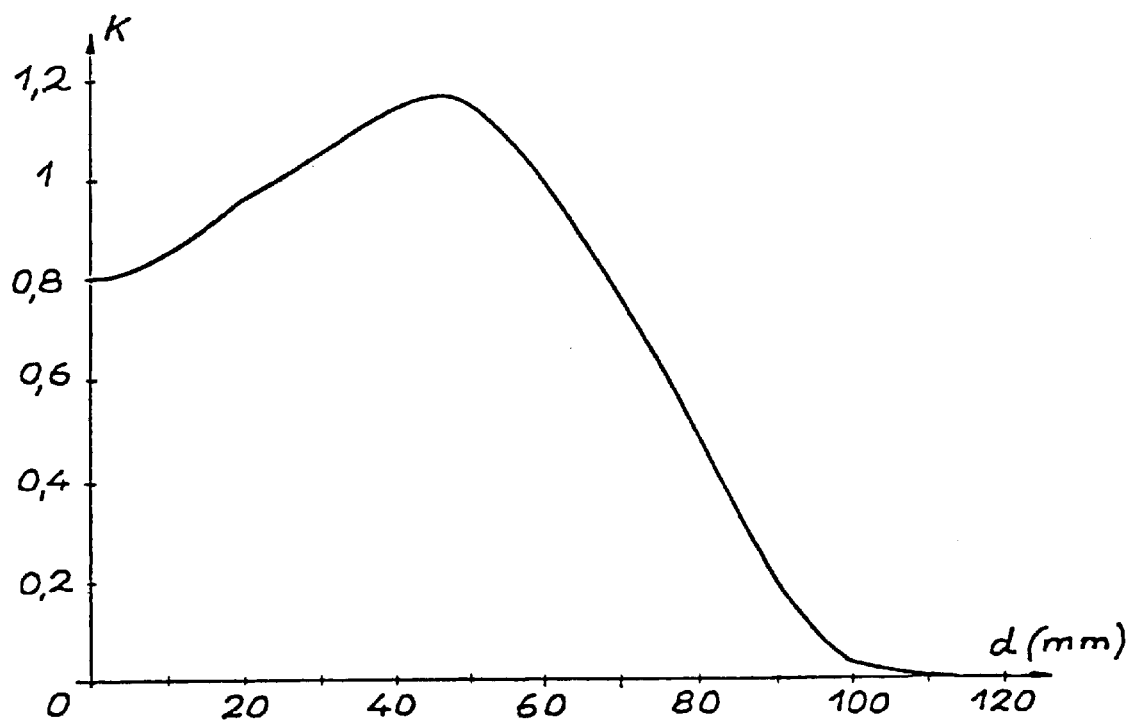
FIG._5B

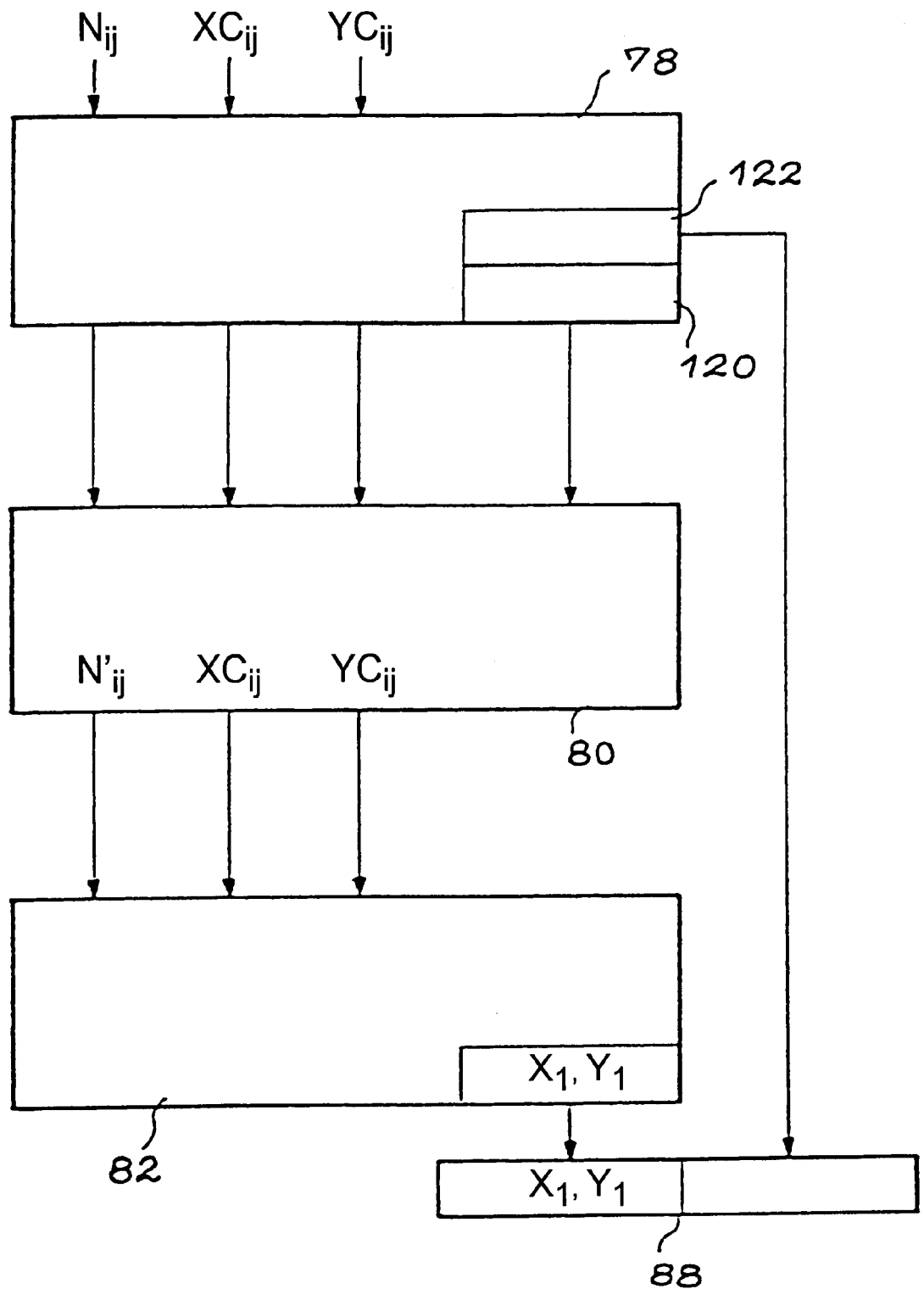
FIG._6

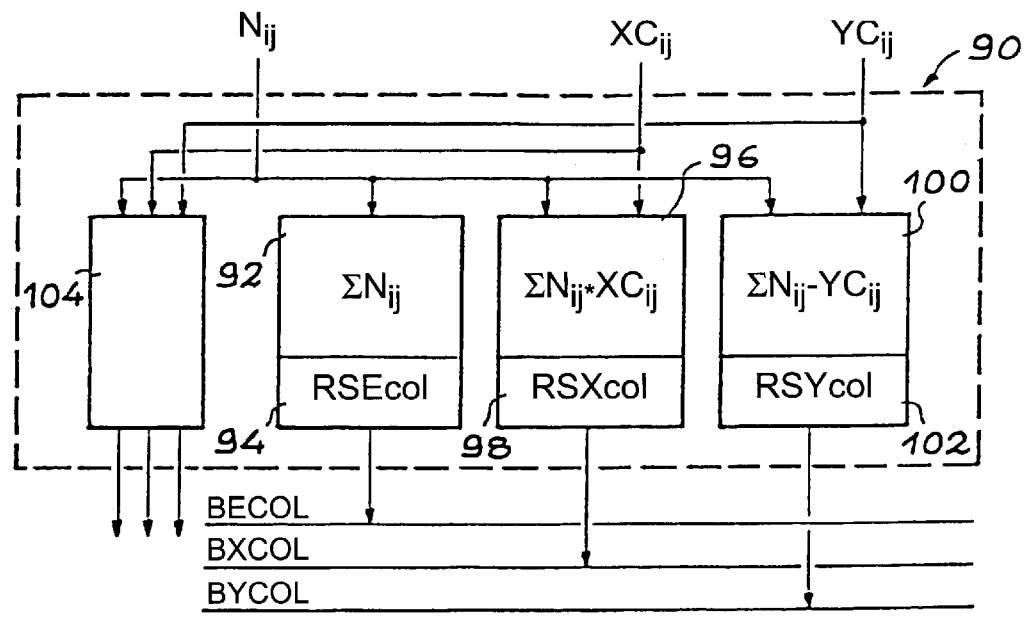
FIG._7
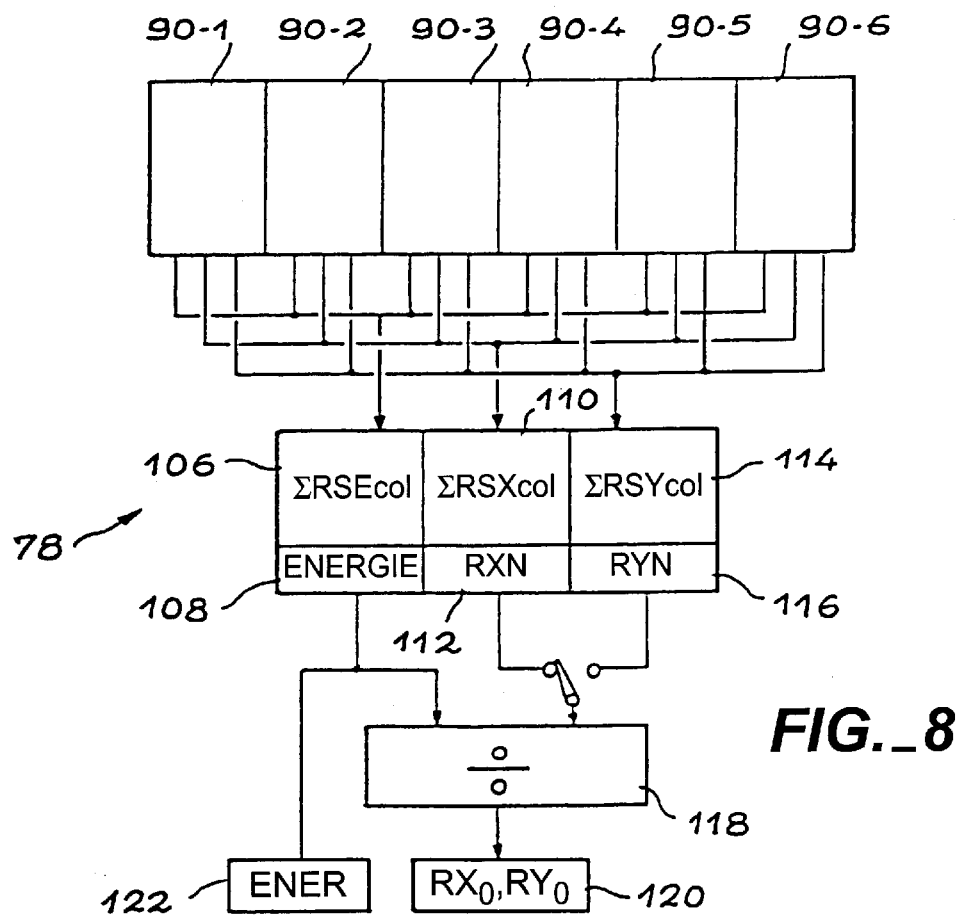
FIG._8

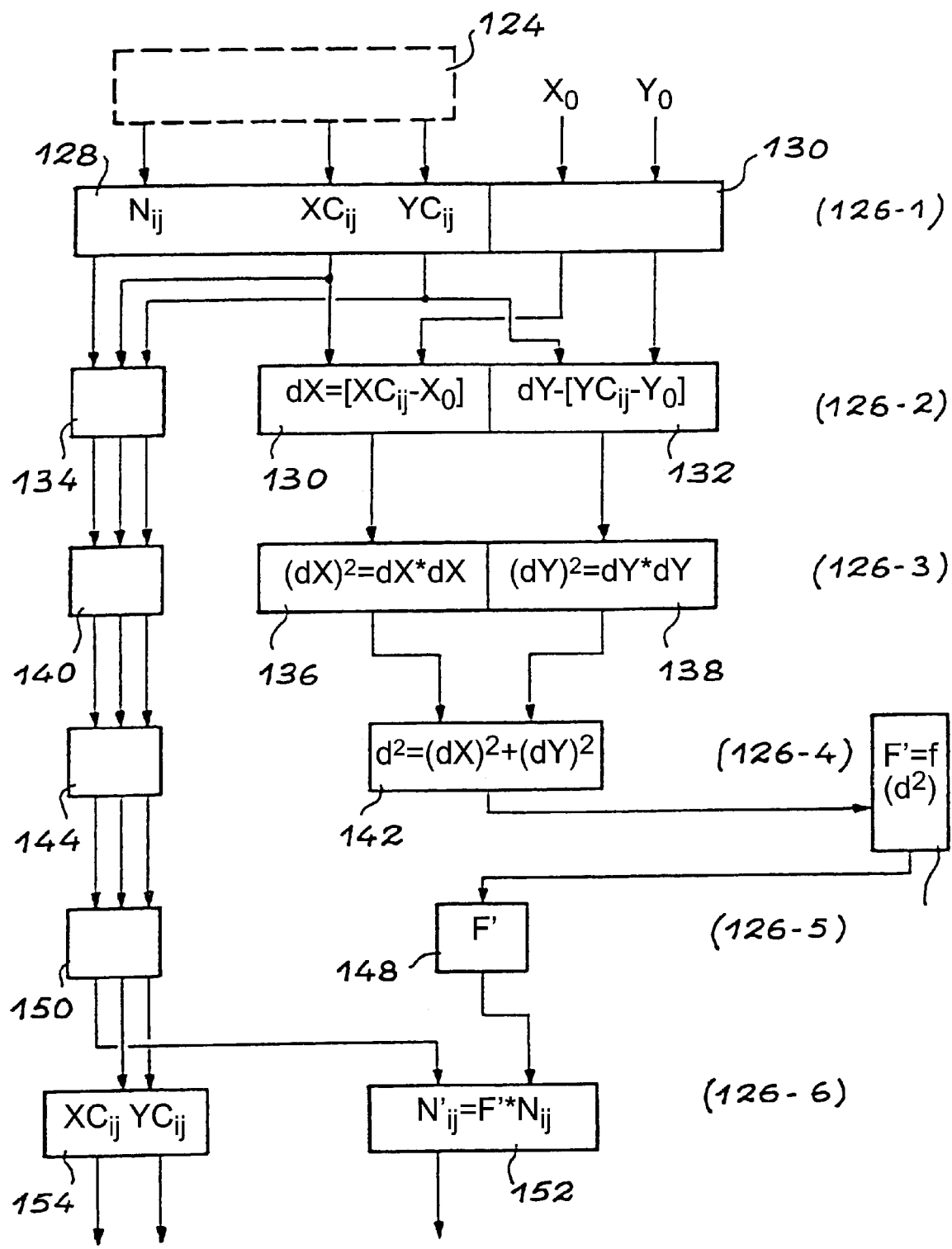
FIG._9

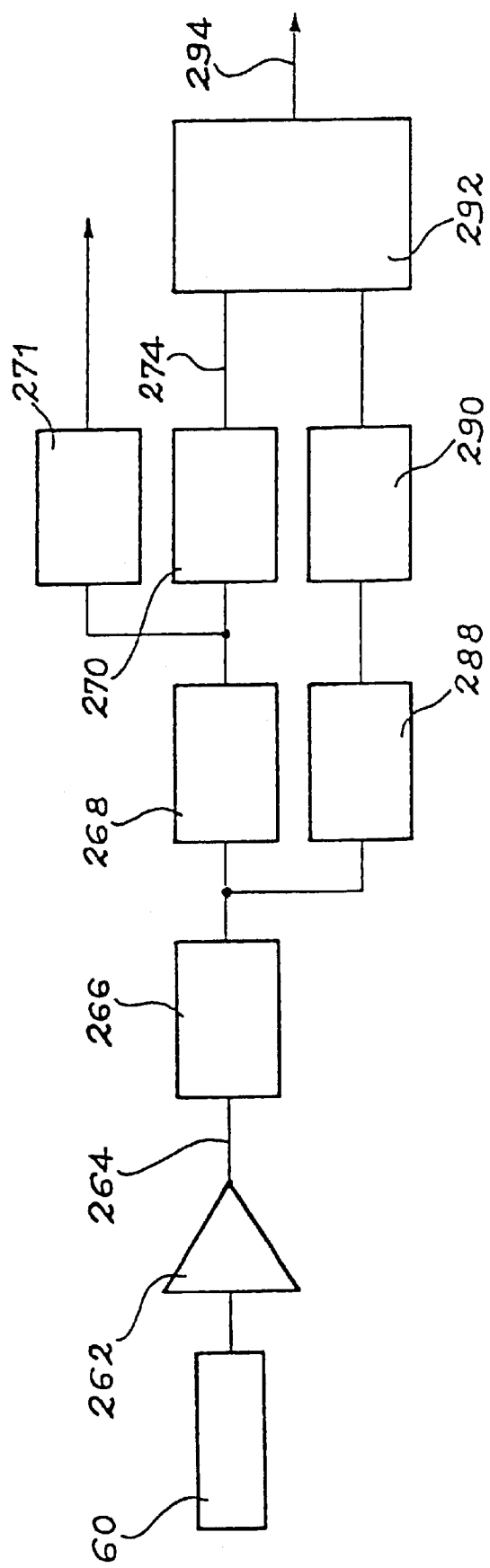
FIG._10

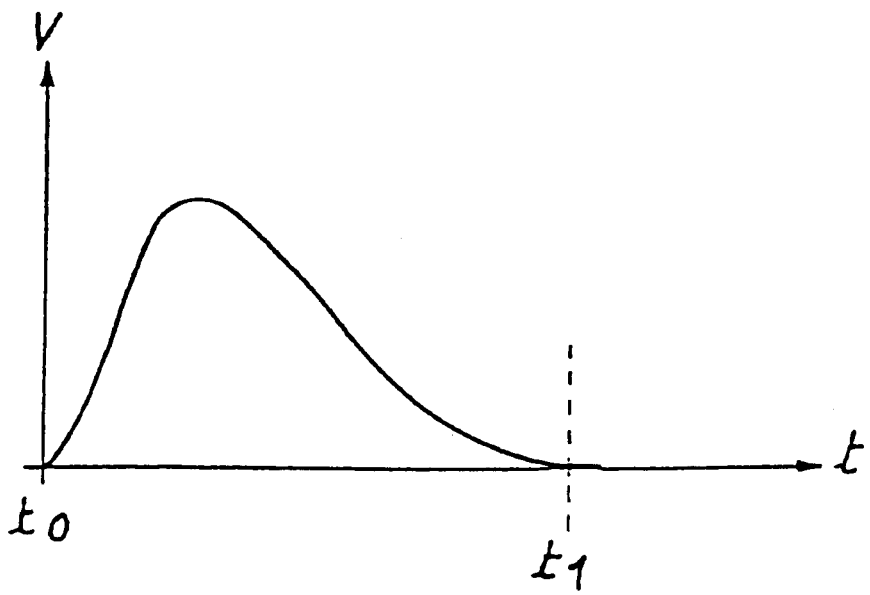
FIG._11A
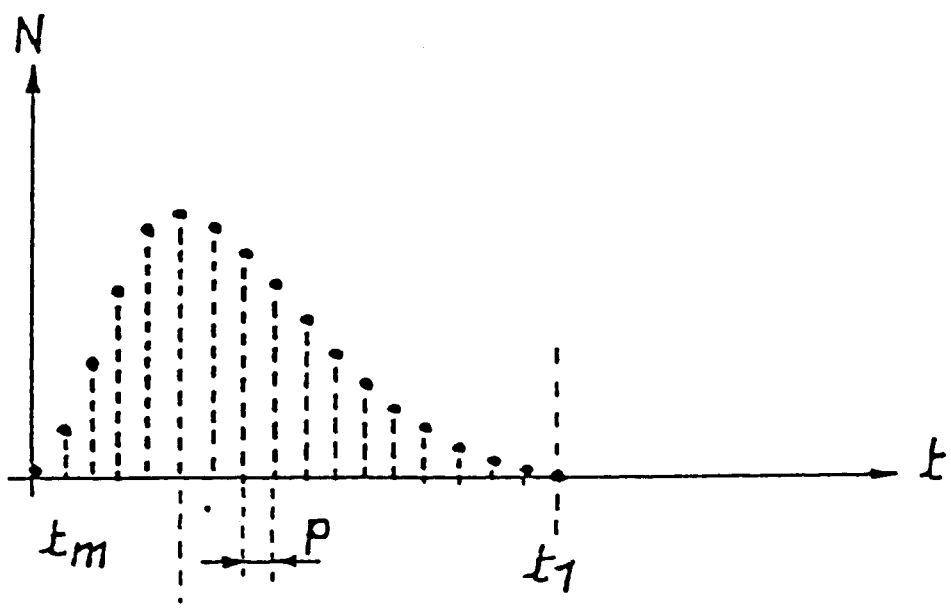
FIG._11B

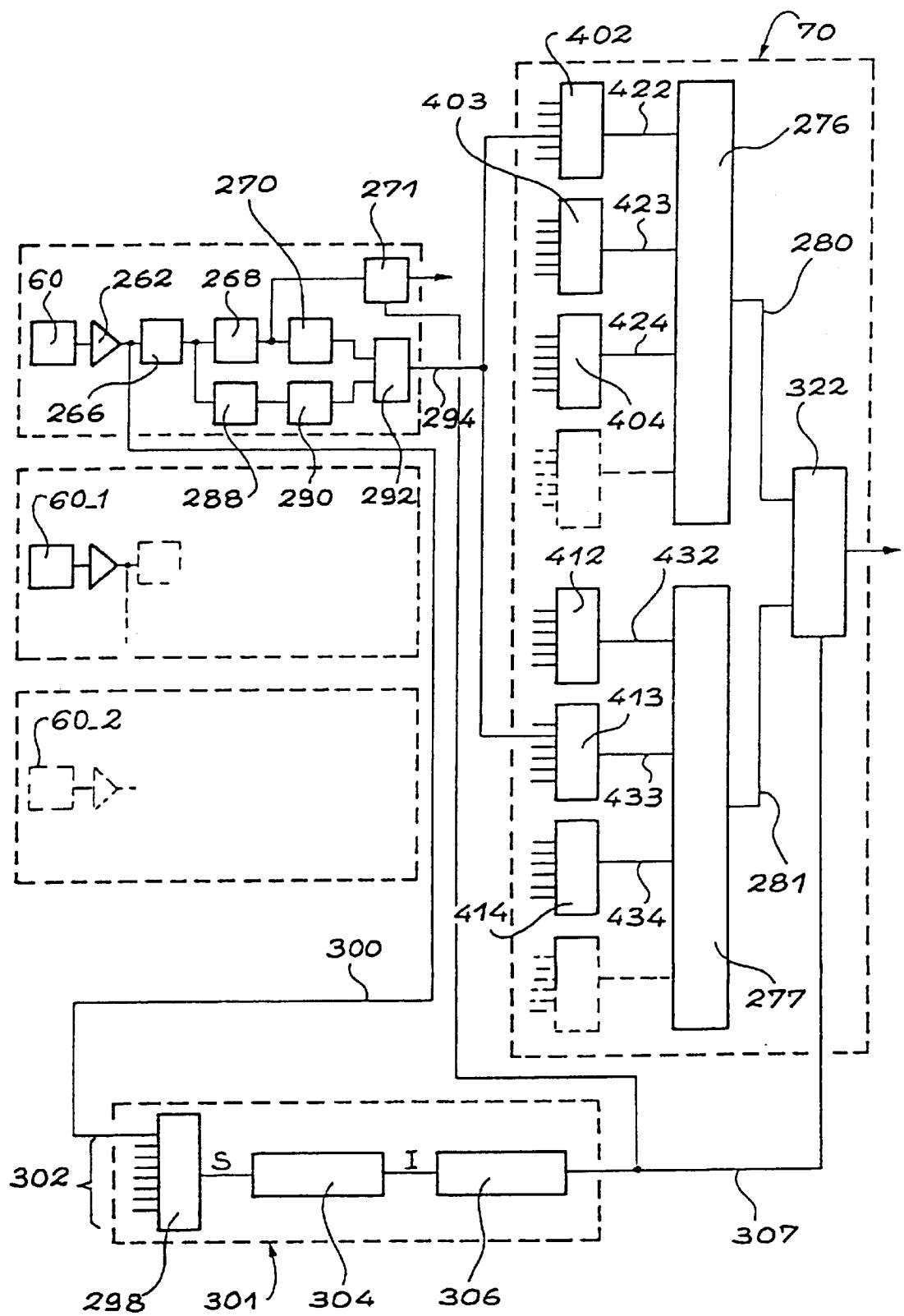
FIG._12 ized with reference to attached FIGS. 2A and 2B.

DEVICE AND METHOD FOR NUCLEAR LOCATING BY ITERATIVE COMPUTING OF BARYCENTER, AND APPLICATION TO GAMMA-CAMERAS

DESCRIPTION

1. Technical Field

This invention relates to a device for determining the position of an event inducing a signal in photodetectors, for example this position being identified with respect to the set of photodetectors. This type of position can be identified by the center of gravity of the event in a coordinate system relative to the photodetectors.

The invention is particularly applicable to determining the position of an event starting from signals output by photo-multipliers used in a gamma-camera, the position being identified with respect to the photo-multipliers themselves. A gamma-camera is a camera that is sensitive to gamma (γ) radiation. This type of camera is used particularly for medical imagery purposes.

2. State of Prior Art

At the present time, most gamma-cameras used in nuclear medicine operate using the principle of Anger type cameras. Document U.S. Pat. No. 3,011,057 provides further information about this subject.

Gamma-cameras have the specific feature that they display the distribution of molecules marked by a radioactive isotope previously injected into the patient, within an organ.

The structure and operation of a known gamma-camera are described and summarized below with reference to the attached FIGS. 1, 2A and 2B.

FIG. 1 shows a detection head 10 of a gamma-camera placed facing an organ 12 containing molecules marked by a radioactive isotope.

The detection head 10 comprises a collimator 20, a scintillator crystal 22, a light guide 24 and several photo-multiplier tubes 26 placed adjacent to each other so as to cover one surface of the light guide 24. For example, the scintillator may be an NaI(Tl) crystal.

The function of the collimator 20 is to select the radiation which reaches the detection head at an approximately normal incidence, among all the gamma radiation 30 emitted by organ 12. The selective nature of the collimator can increase the resolution and the sharpness of the image produced. However, the resolution is increased at the expense of sensitivity. For example, only one photon among about 10 000 γ photons emitted by organ 12, is actually detected.

The γ photons that passed through the collimator arrive at the scintillator crystal 22, where almost all γ photons are converted into several light photons. In the rest of this text, each interaction of a gamma photon with the crystal causing a scintillation is called an event.

Photo-multipliers 26 are designed to emit an electric pulse proportional to the number of light photons received from the scintillator for each event.

In order for a scintillation event to be more precisely positioned, photo-multipliers 26 are not directly fixed to the scintillator crystal 22 but are separated from it by the light guide 24.

Photo-multipliers emit a signal, the amplitude of which is proportional to the total quantity of light produced in the scintillator by gamma radiation, in other words proportional to its energy. However, the individual signal from each photo-multiplier also depends on the distance that separates it from the point 30 at which the gamma radiation interacts with the scintillator material. Each photo-multiplier outputs a current pulse proportional to the light flux that it received. In the example in FIG. 1, small graphs A, B and C show that photo-multipliers 26a, 26b and 26c located at different distances from an interaction point 30 output signals with different amplitudes.

The position of the interaction point 30 of a gamma photon is calculated in the gamma-camera starting from signals originating from the set of photo-multipliers by taking a center of gravity weighting of the contributions of each photo-multiplier.

The principle of center of gravity weighting as used in Anger type cameras can be explained more clearly with reference to attached FIGS. 2A and 2B.

FIG. 2A shows the electric wiring of a gamma-camera detection head 10, that connects this camera to an image generation unit. The detection head comprises several photo-multipliers 26.

As shown in FIG. 2B, each photo-multiplier 26 in the detection head is associated with four resistances denoted $RX^-$, $RX^+$, $RY^-$ and $RY^+$. The values of these resistances are specific to each photo-multiplier and depend on the position of the photo-multiplier in the detection head 10.

Resistances $RX^-$, $RX^+$, $RY^-$ and $RY^+$ in each photo-multiplier are connected to the output 50 of the said photo-multiplier, represented in FIG. 2B by a current generator symbol. They are also connected to common collecting rows denoted $LX^-$, $LX^+$, $LY^-$ and $LY^+$ respectively in FIG. 2A.

Rows $LX^-$, $LX^+$, $LY^-$ and $LY^+$ are in turn connected to analog integrators $52X^-$, $52X^+$, $52Y^-$ and $52Y^+$ respectively, and through these integrators to analog/digital converters $54X^-$, $54X^+$, $54Y^-$ and $54Y^+$ respectively. The output from converters $54X^-$, $54X^+$, $54Y^-$ and $54Y^+$ is directed towards a digital operator 56. Rows $LX^-$, $LX^+$, $LY^-$ and $LY^+$ are also connected to a common channel, called the energy channel. This channel also comprises an integrator 57 and an analog/digital converter 58, and its output is also directed towards operator 56.

The device in FIG. 2 is used to calculate the position of the interaction according to the following equations (U.S. Pat. No. 4,672,542):

$$X = \frac{X^+ - X^-}{X^+ + X^-} \quad \text{and} \quad Y = \frac{Y^+ - Y^-}{Y^+ + Y^-}$$

in which X and Y are the coordinates along two orthogonal directions of the position of the interaction on the crystal, and in which $X^+$, $X^-$, $Y^+$, $Y^-$ represent the weighted signals output by integrators $52X^+$, $52X^-$, $52Y^+$, $52Y^-$ respectively.

The values of X and Y, and the total energy E of the gamma ray that interacted with the crystal, are established by the digital operator 56. These values are then used to generate an image, for example as described in document FR-2 669 439.

The calculation of the interaction position is affected by an uncertainty related to Poisson statistical fluctuations in the number of light photons and the number of photoelectrons produced for each event, in other words for each detected gamma photon. The standard deviation of the fluctuation reduces when the number of photons or photoelectrons increases. Due to this phenomenon, light should be collected as carefully as possible. The intrinsic spatial resolution of the camera is characterized by the width at the mid-height of the distribution of positions calculated for the same collimated point source placed on the scintillator crystal.

The resolution for gamma rays with an energy of 140 keV is usually of the order of 3 to 4 mm.

The energy of a detected gamma photon is calculated by taking the sum of the contributions of all photo-multipliers that received light. It is also affected by a statistical fluctuation. The energy resolution of the camera is characterized by the ratio of the width at the mid-height of the distribution of calculated energies, to the average value of the distribution, for the same source.

The energy resolution is usually of the order of 9 to 11% for gamma rays with an energy of 140 keV.

Finally, an Anger type gamma-camera has the advantage that it enables real time calculation of the center of gravity of photo-multiplier signals with very simple means.

The system described above has a limited number of components. Furthermore, the resistances used to inject the photo-multiplier signal in collecting rows are not very expensive.

However, this type of camera also has a major disadvantage, which is a low count rate. The count rate is the number of events, in other words the number of interactions between a γ photon and the scintillator, that the camera is capable of processing per unit time.

One of the limitations in the count rate is particularly due to the fact that the camera is incapable of processing two events that take place approximately simultaneously at distinct points in the scintillator crystal.

Simultaneous but geometrically distinct events create electrical signals that are stacked in the $LX^-$, $LX^+$, $LY^-$ and $LY^+$ collecting rows and which can no longer be distinguished. These events are also "lost" for the formation of an image.

The limitation in the count rate is not an excessive constraint in traditional medical imagery techniques. As mentioned above, the collimator stops a very large number of gamma rays and only a small number of events are actually detected.

However, gamma cameras are also used in two other medical imagery techniques in which the limitation of the count rate is an unacceptable constraint.

These techniques are called "correction of transmission attenuation" and "coincident PET" (Positron Emission Tomography).

The correction of transmission attenuation technique consists of taking account of the attenuation specific to the tissue of the patient surrounding the examined organ, during the formation of a medical image. In order to determine this attenuation, the transmission of gamma radiation through the patient's body to a gamma-camera is measured. This is done by putting the patient between a highly active external source and the gamma-camera detection head. Thus when measuring the transmitted radiation, a large number of events take place in the scintillator crystal. The large number of events per unit time also increase the probability of having several almost simultaneous events. A conventional Anger type camera is then not suitable.

The PET technique consists of injecting an element such as $F^{18}$ into the patient, capable of emitting positrons. The neutralization of a positron and an electron releases two γ photons emitted in opposite directions with an energy of 511 keV. The PET imagery technique makes use of this physical phenomenon, by using a gamma-camera with at least two detection heads placed on each side of the patient. The detection heads used are not equipped with a collimator. Electronic information processing, called coincidence processing, selects events that occur at the same time, and thus calculates the trajectory of gamma photons.

Therefore, detection heads are subjected to high gamma radiation fluxes. The count rate of conventional Anger type gamma-cameras is usually too limited for this type of application.

For guidance, an Anger type gamma-camera can operate normally with a detection of $1 \times 10^5$ events per second, although in PET imagery at least $1 \times 10^6$ events per second are necessary for normal operation.

Another limitation of Anger type gamma-cameras described above, is due to the fact that the calculation of the center of gravity of an event is fixed by the construction of the detection head and cannot be changed, and particularly by the choice of the resistances $RX^-$, $RX^+$, $RY^-$, $RY^+$, for each photo-multiplier. Similarly, the energy calculation is fixed by wiring photo-multipliers on a common channel (energy channel).

Therefore, devices and processes need to be developed to enable use of gamma-cameras with a high count rate.

Furthermore, it is required to develop cameras for which determination of the center of gravity or location of an event have good linearity and spatial resolution characteristics.

DISCLOSURE OF THE INVENTION

The purpose of the invention is a process for determination of the position $P_0$ of an event with respect to a set of N photodetectors, this event inducing a signal in the N photodetectors, and this process comprising the following steps:

a) a step in which the signal output by each photodetector is digitized, and a value $N_{i,j}$ representing the energy of the signal output by each photodetector is calculated, b) calculate an uncorrected position $P_0$ of the event with respect to the set of photodetectors as a function of values of $N_{ij}$ and the position of the photodetectors, c) determine the distance $d_{i,j}$ of each photodetector with respect to the position $P_0$, d) calculate a corrected value of $N'_{i,j}=F(N_{ij})$, where F is a function that:

reduces (or does not modify) the value $N_{ij}$ for the photodetector corresponding to $P_0$ and for a given number $N_1$ of photodetectors around $P_0$ (for example the $N_1$ first ring photodetectors), increases, or does not modify (or increases) the value $N_{ij}$ for a given number $N_2$ of photodetectors located around the $N_1$ previous photodetectors (for example the $N_2$ second ring photodetectors if the $N_1$ photodetectors are in the first ring; and first ring photodetectors, or the first and second ring photodetectors if $N_1=0$), tends towards 0 at higher values, e) calculate a new position $P_1$ of the event, as a function of the position of the photodetectors and values of $N_{i,j}$.

This type of process can be used to process digitized data, and to produce a position signal $P_1$ of the event with respect to the set of N photodetectors.

The iterative nature of the process according to the invention gives it good spatial resolution and good linearity.

The uncorrected position $P_0$ of the event may be calculated by calculating the coordinates $(X_0, Y_0)$ of center of gravity of the said event as a function of the values of $N_{i,j}$ and the position $(XC_{i,j}, YC_{i,j})$ of each photodetector.

Similarly, the position $P_1$ of the event may be calculated by calculating the coordinates of the center of gravity $(X_1, Y_1)$ of the said event as a function of the values of $N_{i,j}$ and the position $(XC_{i,j}, YC_{i,j})$ of each photodetector.

Due to the choice of the function F, the process according to the invention reduces the contribution of the photodetector located facing the presumed position of the event (and possibly a number $N_1$ of photodetectors around it); this or these photodetectors provide little information about the value of the position, or the center of gravity of the event. Furthermore, this function F assigns greater importance to photodetectors located beyond the photodetector that corresponds to the unweighted position $P_0$ of the event and the $N_1$ photodetectors.

For example, we could choose $N_1=0$ or $N_1=8$ (first ring, particularly for a square distribution of photodetectors).

One particular processing may be done for the photodetectors located at the edge of the field of N photodetectors. This processing consists of the following additional step; modify the value of the position $(Xc_{i,j}, YC_{i,j})$ to a new value $(XC'_{i,j}, YC'_{i,j})$, at least one of the values $|X'|$ and $|Y'|$ being greater than $|X|$ and $|Y|$. Thus the weight and also the position of photodetectors close to the edge of the field will be modified; the process according to the invention simultaneously modifies their contribution and their weight in the calculation of the position or the center of gravity of the event; this enables a magnification of the field and an improvement in the linearity.

The center of gravity calculations may be done sequentially. Processing time is then longer when the number of photodetectors involved in the calculation is greater.

Alternatively, it would be possible to carry out parallel processing of the data. Thus, the coordinates $(X_0, Y_0)$ of the center of gravity of the event could be determined using the following sub-steps:

$b_1$) a sub-step in which the following are determined for each column i:
the contribution of the column to the total energy induced by the event in the set of photodetectors,
the contribution of the column to the X value of the center of gravity of the event,
the contribution of the column to the Y value of the center of gravity of the event, $b_2$) a sub-step in which the following are determined:
the total energy induced by the event in the set of photo-detectors,
the coordinates of the center of gravity $(X_0, Y_0)$ of the event with respect to the N photo-detectors.

The process according to the invention can then be used for the operation of gamma cameras with a high count rate, which is very advantageous for the case of "attenuation correction by transmission" or "coincident PET" measurements. The high count rate is achieved without restricting the number of photo-detectors read. This is due to the parallelism used and the strong pipelining, in other words the sequence of simple operations. The process according to the invention can then be used to accelerate the calculation of the center of gravity of digitized contributions of photodetectors by having this calculation carried out in parallel.

The same parallel processing may be applied to determine the coordinates of the center of gravity $(X_1, Y_1)$ of the event, with the same advantages.

Obviously, columns could be replaced by rows within this invention, the calculation principles being unchanged.

It would be possible to carry out a preliminary step to detect the presumed position of an event. In this case, a subset of N' photo-detectors among the N photo-detectors could be delimited around this presumed position, only the signals from these N' photo-detectors being used to carry out steps b, c, d and e in the process according to the invention.

The invention is applicable particularly advantageously when the photo-detectors are photo-multipliers in a gamma-camera. In particular, imagery techniques in correction of a transmission attenuation, and coincident PET imagery techniques, could be used.

Another purpose of the invention is a device for embodiment of the process described above.

BRIEF DESCRIPTION OF THE FIGURES

In any case, the characteristics and advantages of the invention will become clearer after reading the following description. This description applies to example embodiments given for explanatory purposes and in no way restrictive, with reference to the attached drawings, in which:

FIG. 1, described above, is a diagrammatic section through a detection head of a known type of Anger camera;

FIG. 2 described above, diagrammatically shows a device for collecting and encoding signals originating from photomultipliers in the detection head according to FIG. 1;

FIG. 3 shows the interconnection of a set of photo-detectors;

FIG. 4 shows a device for reading a set of photo-detectors, for an embodiment of the invention;

FIGS. 5A and 5B show examples of function F;

FIG. 6 shows the structure of a calculation system for an embodiment of the invention;

FIG. 7 shows the structure of a column operator for an embodiment of the invention;

FIG. 8 shows the structure of a part of a calculation system for an embodiment of the invention;

FIG. 9 shows an embodiment of another part of a calculation system for an embodiment of the invention;

FIG. 10 shows a circuit associated with the photodetector for processing of data from this photodetector;

FIGS. 11A and 11B show an analog signal output by a photodetector (FIG. 10A), and the corresponding digitized analog signal (FIG. 10B);

FIG. 12 shows an embodiment of a device for determining the presumed position of an event.

DETAILED DESCRIPTION OF EMBODIMENTS OF THE INVENTION

The invention will be described in a detailed manner for the photo-multipliers in a gamma-camera. However, this description is equally valid for any photodetectors, not necessarily forming part of a gamma-camera.

FIG. 3 shows a set of photo-multipliers 60, 60-1, 60-2, etc., making up a gamma-camera head. Each photo-multiplier is identified by its position $(i,j)$ in the set of photo-multipliers. More precisely, the coordinates along the two axes X, Y of the center of photo-multiplier i, j, are denoted $Xc_{i,j}$ and $YC_{i,j}$.

The signal output from each photo-multiplier is digitized and processed individually (integration, corrections, etc.). Each photo-multiplier has a storage register level that is used to memorize the contribution of each photo-multiplier when an event is detected. These aspects will be described later in relation to FIGS. 10–11B.

The photo-multipliers network is organized in rows and columns, and all outputs from photo-multipliers storage registers in the same column are connected to a bus 62 (column bus). Column buses may be collected in one serial bus 64.

An operator carrying out the various steps in the process according to the invention may be connected to the serial bus. This operator then works in series, the processing time being longer if the number of photodetectors involved in the calculation is greater.

A parallel processing could also be considered; an operator carrying out the various steps in the process according to the invention is connected to the column buses 62. This would then give a better count rate.

When the photo-multipliers network is not too large, the set of photo-multipliers can be used.

However when the photo-multipliers network is large (for example between 50 and 100 photo-multipliers), an approximate position of the event is determined first, for example using a method that will be described later with relation to FIG. 12.

The fact of knowing the interaction area of the event already limits the number of photo-multipliers that have to be used to calculate the position of the interaction. In fact, usually only the two photo-multiplier rings that surround the photo-multiplier at which the interaction occurs contain any significant information.

Since the precision of the presumed position is inadequate, it is often necessary to read a larger area than is strictly necessary (for example often up to 25 or 30 reads per event). The time necessary to read storage registers to process an event is a compulsory operation that has a direct influence on the count rate of the machine (number of events processed per second).

In the case of parallel processing, means 66 are provided for selecting each column independently from the others. These means 66 may for example be controlled by a read sequencer 68 (FIG. 4).

FIG. 4 more precisely illustrates the device for embodiment of parallel processing.

A read sequencer 68 reads the contents of the storage register for each photo-multiplier. Let $N_{i,j}$ be the contents of the storage register for the photo-multiplier for column i and row j. $N_{i,j}$ may actually represent a digital integral of the signal output by the photo-multiplier i, j in response to an event.

Means 70 determine a presumed or coarse position of the event. These means will be described later in more detail (FIG. 12).

The read sequencer 68 controls addressing of columns by a multiplexer 74. The contribution of each column to the total energy, to the X component of the center of gravity (XC) and the Y component of the center of gravity (YC) is transferred to a calculation system 76 either by addressing of the columns through the multiplexer, or directly through the calculation sequencer 68.

The number of columns and rows used around each presumed position is imposed by the lack of accuracy of the determination. In FIGS. 4, 36 (6×6) photo-multipliers are used. In general, for a field of N photo-multipliers, it will be necessary to take account of $N_1$ photo-multipliers ($N_1$<N) depending on the required precision; in FIG. 4, N=11×9 and $N_1$=6×6.

Consequently, there is a presumed position (PP) corresponding to each event, and a set of $N_1$ (36) photo-multipliers located on 6 successive rows and 6 successive columns is made to correspond to each presumed position, such that all photo-multipliers in which information is stored are selected. The read sequencer 68 supplies the following at each read step (every 100 nsec) as a function of the presumed position:

commands necessary to the multiplexer 74 so that it can orient the column buses to be read towards the calculation device 76, row selection signals so as to present the storage registers controlled by row n on column buses for the first read times, and then storage registers controlled by row n+1 for the second read time, and so on until reading row n+5 for the sixth read time, the coordinates XC and YC of the centers of the photo-multipliers presented on the column buses.

The sequencer may be made in the form of an EPROM. A memory page corresponds to each presumed position, and the commands and values necessary for the calculation are described in this memory page. This page is read row by row using a counter 72 that activates the low addresses of the EPROMs.

The energy and/or the uncorrected position $P_0$, in X and Y, of an event can be summarized as follows: α) The energy of the event is the sum of the contributions of all photo-multipliers that surround the presumed position:

$$E = \sum_{i,j} N_{i,j}$$

This expression can also be written:

$$E = \sum_i \left[ \sum_j N_{i,j} \right],$$

where $$\sum_j N_{i,j}$$

is the sum of the contributions of the six photo-multipliers in column i, the energy E being the sum of the energies obtained on the six columns.

β) The position $P_0$ of the event is calculated using the center of gravity method:

$$X_0 = \sum_{i,j} (XC_{i,j} * N_{i,j}) \Big/ \sum_{i,j} N_{i,j},$$

where $Xc_{i,j}$ is the X coordinate of the center of the photo-multiplier located on column i and row j, $$Y_0 = \sum_{i,j} (YC_{i,j} * N_{i,j}) \Big/ \sum_{i,j} N_{i,j},$$

where $Yc_{i,j}$ is the Y coordinate of the center of the photo-multiplier located on column i and row j, As above, we can also write:

$$X_0 = \sum_i \left[ \sum_j (XC_{i,j} * N_{i,j}) \right] \Big/ \sum_{i,j} N_{i,j}, \quad \text{where} \quad \sum_j (XC_{i,j} * N_{i,j})$$

is the contribution to the X coordinate of the center of gravity of the 6 photo-multipliers in column i, $$Y_0 = \sum_i \left[ \sum_j (YC_{i,j} * N_{i,j}) \right] / \sum_{i,j} N_{i,j}, \quad \text{where} \quad \sum_j (YC_{i,j} * N_{i,j})$$

is the contribution to the Y coordinate of the center of gravity of the 6 photo-multipliers in column i.

The unweighted center of gravity $P_0$ is the result obtained using steps α) and β) described above, in opposition to the weighted center of gravity.

Once the unweighted center of gravity $P_0(X_0, Y_0)$ is known, the distance $d_{i,j}$, from the center of each photo-multiplier to $P_0$ can be calculated and the value $N_{i,j}$ can be weighted by calculating a new $N_{i,j}$ called $N'_{i,j}$ such that $N'_{i,j}=F(N_{i,j})$ where F is a function of $d_{i,j}$ (weighting function).

This function F is determined empirically and is adapted to each type of photo-multiplier and each light collection geometry.

In general, the function F:

is less than 1 for a small $d_{i,j}$ (to minimize the contribution of the photo-multiplier that receives the event when it is close to its center, this photo-multiplier contributing little to information about the center of gravity), is greater than 1 when $d_{i,j}$ is of the same order of magnitude as the dimension of the photo-multiplier (to increase the contribution of first ring photo-multipliers, in other words photo-multipliers closest to the photo-multiplier that receives the event), tends towards zero when $d_{i,j}$ becomes large (to reduce the contribution of photo-multipliers as the distance increases from the interaction location, since the signal/noise ratio of their contribution deteriorates).

FIG. 5A shows a first example of function F(d) This first example corresponds to 75 mm square photo-multipliers. Values of F for particular values of d (with a 5 mm pitch) are given in table I below:

TABLE I

| d | F |
|---|---|
| 0 | 0.8 |
| 5 | 0.809 |
| 10 | 0.826 |
| 15 | 0.85 |
| 20 | 0.883 |
| 25 | 0.916 |
| 30 | 0.95 |
| 35 | 0.983 |
| 40 | 1.016 |
| 45 | 1.05 |
| 50 | 1.083 |
| 55 | 1.116 |
| 60 | 1.15 |
| 65 | 1.176 |
| 70 | 1.194 |
| 75 | 1.2 |
| 80 | 1.18 |
| 85 | 1.13 |
| 90 | 1 |
| 95 | 0.831 |
| 100 | 0.663 |
| 105 | 0.494 |
| 110 | 0.325 |
| 115 | 0.117 |
| 120 | 0.1 |
| 125 | 0.065 |
| 130 | 0.035 |
| 135 | 0.015 |
| 140 | 0 |

TABLE I-continued

| d | F |
|---|---|
| 145 | 0 |
| 150 | 0 |

FIG. 5B shows a second example of function F(d). This second example is applicable to 60 mm hexagonal photo-multipliers. Values of F for particular values of d (with a pitch of 5 mm) are given in table II below:

TABLE II

| d | F |
|---|---|
| 0 | 0.8 |
| 5 | 0.813 |
| 10 | 0.856 |
| 15 | 0.906 |
| 20 | 0.963 |
| 25 | 1.006 |
| 30 | 1.056 |
| 35 | 1.106 |
| 40 | 1.15 |
| 45 | 1.169 |
| 50 | 1.144 |
| 55 | 1.075 |
| 60 | 0.975 |
| 65 | 0.863 |
| 70 | 0.744 |
| 75 | 0.619 |
| 80 | 0.475 |
| 85 | 0.319 |
| 90 | 0.181 |
| 95 | 0.081 |
| 100 | 0.025 |
| 105 | 0.013 |
| 110 | 0 |
| 115 | 0 |
| 120 | 0 |

From the production point of view, the calculation of the weighted center of gravity $P_1$ is made in the same way as for the unweighted center of gravity $P_0$, after having replaced $N_{i,j}$ by $N'_{i,j}$. The unweighted center of gravity calculation is followed by a weighting operation using function F.

A calculation device or system 76 for embodiment of the process according to the invention may comprise three sets shown diagrammatically in FIG. 6 and denoted as references 78, 80 and 82 respectively.

The structure of device 78 used to determine $P_0$ will now be described more precisely in relation to FIGS. 7 and 8.

FIG. 7 shows means 90 associated with each column and subsequently denoted the column operator.

In addition to the values $N_{i,j}$ of column photo-multipliers, this device also receives the coordinates $XC_{i,j}$ and $YC_{i,j}$ of the centers of the corresponding photo-multipliers, for example output by the read sequencer 68. The X coordinates are not necessarily identical for the same column, since they must take account of the real position of the photo-multiplier within the field of the gamma-camera. The same is true for the Y coordinates. In the example given, each output from the column bus is connected to the input of a column operator 90.

Each column operator 90 performs three operations, preferably in parallel.

A first operation consists of calculating the contribution of the column to the energy. For example, after being initialized at the beginning of the sequence, an accumulator 92 takes the sum of the values $N_{i,j}$ of the 6 photo-multipliers in the column and stores the result in a register 94 (RSEcol). The outputs from the six registers (RSEcol1 to RSEcol6) are grouped on a common bus BECOL.

A second operation consists of calculating the contribution of the column to the X value of the center of gravity. For example, after being initialized at the beginning of the sequence, a multiplier-accumulator 96 takes the sum of the contributions to the X value of the center of gravity of the 6 photo-multipliers in the column, and stores the result in a register 98 (RSXcol). The outputs from the six registers (RSXcol1 to RSXcol6) are grouped on a common bus BXCOL.

A third operation consists of calculating the contribution of the column to the Y value of the center of gravity. For example, after being initialized, a second multiplier-accumulator 100 takes the sum of the contributions to the Y value of the center of gravity of the 6 photo-multipliers in the column, and stores the result in a register 102 (RSYcol). The outputs from the six registers (RSYcol1 to RSYcol6) are grouped on a common bus BYCOL.

At the end of the 6 read times, the 6 column operators that have completed their work become available for another read since the results of the first read are stored.

In parallel to these calculation operations, the values $N_{i,j}$ of the photo-multipliers and the coordinates $Xc_{i,j}$ and $YC_{i,j}$ may be stored in a FIFO type system 104 so that they can be used later on.

Contributions to the energy and to the coordinates of the X and Y values of the center of gravity are then grouped. This grouping will be described with reference to FIG. 8 in which the references 90-1, . . . , 90-6 denote 6 column operators of the type described above in relation to FIG. 7.

An accumulator 106 is initialized at the beginning of the sequence and receives input through the BECOL bus, and calculates the sum of the six registers RSEcol1 to RSEcol6 and stores the result in a register 108 (ENERGY). The contents of this register represent the sum of the energy contributions of the 36 photo-multipliers surrounding the presumed position, and therefore the energy of the event.

A second accumulator 110 receives input through the BXCOL bus, and calculates the sum of the six registers RSXcol1 to RSXcol6 and stores the result in a register 112 (RXN). The contents of this register represent $$\sum_i \left[ \sum_j (XC_{ij} * N_{ij}) \right].$$

A third accumulator 114 receives input through the BYCOL bus, and calculates the sum of the six registers RSYcol1 to RSYcol6 and stores the result in a register 116 (RYN). The contents of this register represent $$\sum_i \left[ \sum_j (YC_{ij} * N_{ij}) \right].$$

The RSEcol, RSXcol and RSYcol registers are then released so that they can be used by column operators, and the accumulators are thus once again available to process another event.

Finally, the $X_0$ and $Y_0$ coordinates of the interaction point $P_0$ of the event are calculated by making two divisions using a divider 118:

$X_0$=RXN/ENERGY, and $Y_0$=RYN/ENERGY, in less than 6 read times so that storage registers 108, 112, 116 can be released. Commercially available integrated pipelined dividers (for example such as the RAYTHEON 3211) are easily capable of achieving these performances and it is even possible to use a single package by making the two divisions in sequence.

Therefore, the position $P_0$ of the event is obtained, and the $X_0$ and $Y_0$ coordinates of this position are stored in a register 120 ($RX_0$ and $RY_0$). At the same time as the divisions, the energy may be pipelined from register 108 to a register 122 in order to release register 108 for the next event.

FIG. 9 contains a simple embodiment of the device 80 (calculation of the weighted center of gravity—FIG. 6).

The values of $N_{i,j}$, $Xc_{i,j}$, $YC_{i,j}$ that were used in the calculation of the unweighted center of gravity have been stored in the FIFO memories denoted globally as reference 124 (the memory 104 (FIG. 7) in which $N_{i,j}$ is stored was already mentioned above). The calculation is organized in steps 126-1, . . . , 126-6 described below, for each weighting operator operating on a column:

126-1: retrieve the first value $N_{i,j}$ and the coordinates of the center of the corresponding photo-multiplier $XC_{i,j}$ and $YC_{i,j}$ (first value written in the FIFO and therefore first value read) and store the weighting operator in an input register 128. At the same time the values $X_0$ and $Y_0$ at the input to the operator are stored in memory 130. This storage operation is not repeated for the next 5 acquisitions of $N_{i,j}$, $XC_{i,j}$ and $YC_{i,j}$, since $P_0$ is unchanged.

126-2: calculate $dX=|XC_{i,j}-X_0|$, and at the same time $dY=|YC_{i,j}-Y_0|$, and store dX, dY, $N_{i,j}$, $XC_{i,j}$ and $YC_{i,j}$ in memories 130, 132, 134. The registers used for step 126-1 are then released, and can then be used to contain values for the next photo-multiplier. The next photo-multiplier is then processed in the same way as the previous photo-multiplier and so on until the sixth.

126-3: calculate $(dX)^2=dX*dX$, and at the same time $(dY)^2=DY*DY$, and store $(dX)^2$, $(dY)^2$, $N_{i,j}$, $XC_{i,j}$ and $YC_{i,j}$ in memories 136, 138, 140. The step 126-2 output registers are then released.

126-4: calculate $d=(dX)^2+(dY)^2$ and store $d^2$, $N_{i,j}$, $XC_{i,j}$, and $YC_{i,j}$ in registers 142, 144; the step 126-3 output registers are then released.

126-5: address an EPROM 146 containing the function $F'=f'(d^2)$, through the register containing $d^2$. This avoids the need to extract the square root of $d^2$, knowing that it is easy to obtain $F'=f'(d^2)$ when $F=f(d)$ is known. F', $N_{i,j}$, $XC_{i,j}$ and $YC_{i,j}$ are then stored in registers 148 and 150, and the step 126-4 output registers are then released.

126-6: calculate $N'_{i,j}=F'*N_{i,j}$ and store $N'_{i,j}$, $XC_{i,j}$ and $YC_{i,j}$ in registers 152 and 154; the step 126-5 output registers are then released.

After being broken down and pipelined in this manner, it is easy to calculate $N'_{i,j}$, since each calculation step is sufficiently simple to be carried out during one read step (typically 100 nsec).

The third calculation subsystem 82 (FIG. 6) to calculate the weighted center of gravity $X_1$, $Y_1$, has an architecture of the type described above in relation to FIGS. 7 and 8.

The output of the weighted center of gravity gives the new coordinates $X_1$, $Y_1$ of the position of the event. The value of the energy can be determined at the same time as the calculations are being carried out; the energy and coordinates of the event are obtained in the final output in the same register 88.

We will now describe how the signal output from each photo-multiplier is detected and processed, and in particular how a presumed position of the event can be calculated.

FIG. 10 shows part of the device associated with a single photo-multiplier 60. The photo-multiplier 60 is connected to a current-voltage converter 262. In response to an event detected by the photo-multiplier, a signal is obtained on the output 264 from the current-voltage converter 262, for example of the type illustrated in FIG. 11A.

The ordinate of the graph in FIG. 11A shows the amplitude of the signal corresponding to the pulse, and the abscissa shows the time. The amplitude of the signal and the time are indicated in an arbitrary scale. $t_0$ denotes the start time of the pulse output by the photodetector and $t_1$ denotes the time at which the pulse drops to almost zero, after having passed through a maximum. For guidance, the duration corresponding to the interval $t_1-t_0$ is of the order of one microsecond, in the case of a photo-multiplier of a gamma-camera coupled to an NaI (Tl) crystal.

The analog signal present on the output terminal 264 is directed to an analog-digital converter 266. This converter samples each signal pulse taking a number of samples n as shown in FIG. 10B. Two consecutive samples are separated by a step or clock interval p (the clock operates at 1/p Hz).

For example, the converter samples each signal pulse using n=10 samples. Thus for a 1 microsecond signal, a sample is taken every 100 nanoseconds.

The analog-digital converter 266 is preferably a fast converter of the "flash" type capable of operating at a frequency of the order of 10 to 20 Megahertz.

The digital signal output from the analog-digital converter 266 is directed towards a digital adder 268. This adder takes the sliding sum of the samples sent to it by the analog-digital converter 266. The sliding sum is carried out on a given number of samples. For example, this predetermined number may be equal to 10.

For each photo-detector i,j, this sliding sum, or the digital integral of the signal associated with the event, corresponds to the magnitude $N_{i,j}$, already introduced above.

At the same time, the result of the summation made with means 268 is stored in a register 271. The storage function may be composed of several registers so that several events at very close time intervals can be stored.

The value of the sliding sum is then sent to comparison means 270. These means compare the value of the sliding sum with a predetermined fixed threshold value at an input 272 of comparator 270. This comparator sends a binary signal to output 274 representing the result of the comparison (for example 0 if the value of the sliding sum is less than the fixed reference value, and 1 if the value of the sliding sum is greater than the reference value).

In order to limit the duration of this overshoot, it will only be validated during a time window centered on the maximum of the sliding sum. This separates events that are close in time, but are geographically distinct on the detector field.

This window is positioned by using the time at which the encoded signal passes through a maximum, as a reference. This detection is made by means 288 by comparing the current value of the encoder output with the previous value. When the current value is less than the previous value, the comparator 288 outputs a pulse. This pulse is sent to an offset register 290, in which the delay $n_1$ is adjusted to generate a time window centered on the maximum of the sliding sum. To take account of the inaccuracy (approximately one sampling step) with which the maximum position of the encoded signal is determined, the time window will be activated during no sampling steps, where $n_0 \geq 3$ (for example $n_0=3$), this choice of a minimum of three minimizing simultaneous signals exceeding the threshold between photo-multipliers activated by the same event.

The signal obtained at the output from comparator 270 and the output signal from the offset register 290 are applied as inputs to an AND gate 292, which produces a threshold overshoot signal on its output 294 at the required instant with respect to the digital signal passing through a maximum.

FIG. 12 shows a device according to the invention for processing signals output from several photodetectors 60, 60-1, 60-2. In this figure, references identical to the references in FIG. 10 denote similar or corresponding elements.

In this figure, it can be seen that an analog signal 300 of the type described above with relation to FIG. 11A can be taken from the output of the current-voltage converter 262. In FIG. 12, reference 302 globally denotes all analog signals taken from other current-voltage converters 262-1, 262-2, etc. All these signals are input into an analog adder 298 that outputs a signal S which is the sum of all analog signals output by a given number of photodetectors, for example by all photodetectors. A device 304 outputs a pulse I when the signal S passes through its maximum. For example, this device 304 comprises a differentiator (capacitor, amplifier and resistances between the amplifier input and output); the output from this differentiator is input into a comparator that detects when the differentiator output changes to 0. Pulse I is input into an offset register 306 that uses a step p that is controlled by clock H. The output 307 from this register is called a storage pulse and in particular triggers the storage register 271 corresponding to photodetector 60. It also triggers each storage register associated with each photodetector. The delay in the offset register 306 is adjusted so that the rising front of the storage signal 307 is synchronous with the moment at which the sums must be stored in registers 271.

For example, the set of photodetectors 60, 60-1, 60-2 ※ may be distributed in a two-dimensional network.

In order to mark the presumed position (or the approximate position) of an event with respect to this two-dimensional photodetectors network, it is advantageous to associate a read access memory with a first coordinate direction in the photodetectors network, and a read access memory with a second coordinate direction in the photodetectors network. If this network is identified by rows and columns, one read access memory can be associated to identify a "row" coordinate, and one read access memory can be used to identify a "column" coordinate.

More precisely, in a device according to the invention of the type illustrated in FIG. 12, the outputs 294 that represent photodetectors at the center of the interaction (when the outputs are active) are used as follows:

an OR circuit (402) contains type 294 outputs from the photo-detectors in a single column and generates an active signal 422 when at least one of its inputs is active. There is one 402 type circuit for each column, an OR circuit (412) contains type 294 outputs from the photo-detectors in a single row and generates an active signal 432 when at least one of its inputs is active. There is one 412 type circuit for each row.

Type 422 signals are the addresses of a PROM 276 that is programmed to output the coordinate (280) of the presumed position with respect to the columns. Similarly, type 432 signals are the addresses of a second PROM 277 that is programmed to output the coordinates (281) of the presumed position with respect to the rows. The presumed position represented by the pair of values (280, 281) is stored in a register 322, at the same time as the contributions of all photodetectors are stored in their corresponding registers (271). This storage operation is triggered by the signal 307 generated by register 306.

What is claimed is:

1. Process for determining the position of an event with respect to a set of N photodetectors, comprising the following steps:
   a) digitize the signal output by each photodetector, and calculate a value $N_{i,j}$ representing the energy of the signal output by each photodetector,
   b) calculate an uncorrected position $P_0$ of the event with respect to the set of photodetectors, as a function of values $N_{i,j}$ and the position of the photodetectors,
   c) determine the distance $d_{i,j}$ of each photodetector with respect to the position $P_0$,
   d) calculate a corrected value of $N_{i,j}=F'(N_{ij})$, where F' is a function that:
      reduces (or does not modify) the value $N_{ij}$ for the photodetector corresponding to $P_0$ and for a given number $N_1$ of photodetectors around $P_0$,
      increases, or does not modify (or increases) the value $N_{ij}$ for a given number $N_2$ of photodetectors located around the $N_1$ previous photodetectors,
      tends towards 0 at higher values,
   e) calculate a new position $P_1$ of the event, as a function of the position of the photodetectors and values of $N'_{i,j}$.

2. Process according to claim 1, in which the uncorrected position $P_0$ of the event is calculated by calculating the coordinates $(X_0, Y_0)$ of the center of gravity of the said event as a function of $N_{i,j}$ and the position $(XC_{i,j}, YC_{i,j})$ of each photodetector.

3. Process according to claim 2, the center of gravity calculations being carried out in sequence.

4. Process according to claim 2, in which the coordinates $(X_0, Y_0)$ of the center of gravity of the event are determined using the following substeps:
   $b_1$) a sub-step in which the following are determined for each column i:
      the contribution of the column to the total energy induced by the event in the set of photodetectors,
      the contribution of the column to the X value of the center of gravity of the event,
      the contribution of the column to the Y value of the center of gravity of the event,
   $b_2$) a sub-step in which the following are determined:
      the total energy induced by the event in the set of photo-detectors,
      the coordinates of the center of gravity $(X_0, Y_0)$ of the event with respect to the N photodetectors.

5. Process according to claim 1, in which the position $P_1$ of the event is calculated by calculating the coordinates $(X_1, Y_1)$ of the center of gravity of the said event as a function of $N'_{i,j}$ and the position $(XC_{i,j}, YC_{i,j})$ of each photodetector.

6. Process according to claim 5, in which the coordinates $(X_1, Y_1)$ of the center of gravity of the event could be determined using the following sub-steps:
   $e_1$) a sub-step in which the following are determined for each column i:
      the contribution of the column to the total energy induced by the event in the set of photodetectors,
      the contribution of the column to the X value of the center of gravity of the event,
      the contribution of the column to the Y value of the center of gravity of the event,
   $e_2$) a sub-step in which the following are determined:
      the total energy induced by the event in the set of photodetectors,
      the coordinates of the center of gravity $(X_1, Y_1)$ of the event with respect to the N photodetectors.

7. Process according to claim 1, comprising the following step before step e), for each photodetector at the edge of the field of N photodetectors:
   $e_0$) modify the value of the position $(XC_{i,j}, YC_{i,j})$ the new pair of values $(XC'_{i,j}, YC'_{i,j})$ being such that either the $|XC'_{i,j}|>|XC_{i,j}|$ relation or the $|YC'_{i,j}|>|Yc_{i,j}|$ relation is satisfied, or both of these relations are satisfied.

8. Process according to claim 1, also comprising an additional step prior to step b):
   a') to determine the presumed position of an event.

9. Process according to claim 8, also comprising a step:
   $a'_2$) to delimit a subset of N' photodetectors among the set of N photodetectors around the presumed position of the event, only the signals from the N' photodetectors in this subset being processed according to steps b, c, d and e.

10. Process according to claim 1, the photodetectors being photo multipliers of a gamma-camera.

11. Imagery process in correction of transmission attenuation, embodying the process according to claim 10.

12. PET coincidence imagery process embodying the process according to claim 10.

13. Device for determining the position of an event, particulary with respect to a set of N photodetectors, comprising:
   a) means of digitizing signals output by each photodetector, and of calculating a value $N_{i,j}$ representing the energy of the signal output by each photodetector,
   b) means of calculating an uncorrected position of $P_0$ of the event,
   c) means of determining a distance $d_{i,j}$ of each photodetector relative to the uncorrected position,
   d) means of calculating a corrected value $N'_{i,j}=F'(N_{i,j})$,
   e) means of calculating a new position $P_1$ of the event, said means of calculating a new position means being controlled by the means of calculating the corrected values $N'_{i,j}=F'(N_{i,j})$.

14. Device according to claim 13, the means of calculating the uncorrected position $P_0$ of the event being means of calculating the coordinates of the center of gravity of the said event.

15. Device according to claim 13, the means of calculating the new position $P_1$ of the event, being the means of calculating the center of gravity of this new position.

16. Device according to claim 15, also comprising means for:
   b') determining the following for each column i making use of the values of the weighted signal $N'_{i,j}$:
      the contribution of the column to the total energy induced by the event in the set of photodetectors,
      the contribution of the column to the X value of the center of gravity of the event,
      the contribution of the column to the Y value of the center of gravity of the event,
   c') determining the following making use of the values of the contributions obtained in b')
      the total energy induced by the event in the set of photodetectors,
      the new coordinates of the center of gravity $(X_1, Y_1)$ of the event with respect to the N photodetectors.

17. Device according to claim 13, also comprising means:

d') of modifying the value of the position ($XC_{i,j}$, $YC_{i,j}$) of the photodetectors located at the edge of the photodetectors field, to a position ($XC'_{i,j}$, $YC'_{i,j}$) in which the $|XC'_{i,j}|>|XC_{i,j}|$ relation or the $|YC'_{i,j}|>|YC_{i,j}|$ relation is satisfied, or both of these relations are satisfied.

18. Device according to claim 13, also comprising:

a set of N photodetectors laid out in rows and columns, means of grouping the photodetectors in the same column on a column bus, means of grouping the column buses on a serial bus.

19. Device according to claim 18, an operator including all means b) to e) being connected to the serial bus and performing serial processing of the data.

20. Device according to claim 18, an operator including all means b) to e) being connected to the column buses and carrying out parallel processing of the data.

21. Device according to claim 13, comprising means of determining the following for each column i:

the contribution of the column to the total energy induced by the event in the set of photodetectors, the contribution of the column to the X value of the center of gravity of the event, the contribution of the column to the Y value of the center of gravity of the event, and means in which the following are determined:

the total energy induced by the event in the set of photodetectors, the coordinates of the center of gravity ($X_0$, $Y_0$) of the event with respect to the N photodetectors.

22. Device according to claim 13, also comprising means of detecting the presumed position of an event.

23. Device according to claim 22, also comprising means of delimiting a subset of $N_1$ photodetectors among the set of N photodetectors around the presumed position of the event.

24. Device according to claim 13, the photodetectors being the photomultipliers in a gamma-camera.

* * * * *